US006846660B2

(12) United States Patent
Hoshino et al.

(10) Patent No.: US 6,846,660 B2
(45) Date of Patent: Jan. 25, 2005

(54) **METHOD OF MAKING AN ALDEHYDE DEHYDROGENASE WITH *GLUCONOBACTER***

(75) Inventors: Tatsuo Hoshino, Kamakura (JP); Taro Miyazaki, Fujisawa (JP); Teruhide Sugisawa, Yokohama (JP)

(73) Assignee: Roche Vitamins Inc., Parsippany, NJ (US)

( * ) Notice: Subject to any disclaimer, the term of this patent is extended or adjusted under 35 U.S.C. 154(b) by 602 days.

(21) Appl. No.: 09/815,695

(22) Filed: Mar. 23, 2001

(65) Prior Publication Data

US 2001/0026933 A1 Oct. 4, 2001

Related U.S. Application Data

(62) Division of application No. 09/203,628, filed on Dec. 1, 1998, now Pat. No. 6,242,233.

(30) Foreign Application Priority Data

Dec. 1, 1997 (EP) ............................................ 97121089

(51) Int. Cl.[7] ................................................ C12N 9/04
(52) U.S. Cl. ..................... 435/190; 435/136; 435/252.1; 435/191; 435/71.2
(58) Field of Search ................................ 435/190, 136, 435/252.1, 191, 71.2

(56) References Cited

U.S. PATENT DOCUMENTS

| | | | |
|---|---|---|---|
| 3,907,639 | A | 9/1975 | Makover et al. |
| 5,437,989 | A | 8/1995 | Asakura et al. |
| 5,932,463 | A | 8/1999 | Asakura et al. |

FOREIGN PATENT DOCUMENTS

| | | |
|---|---|---|
| EP | 0 278 447 B1 | 7/1993 |
| EP | 0 606 621 A2 | 7/1994 |
| EP | 0 758 679 A1 | 2/1997 |
| EP | 0 790 301 A2 | 8/1997 |

OTHER PUBLICATIONS

Kitamura, et al., "Metabolism of L–Sorbose by Enzymes from *Gluconobacter melanogenus* IFO 3293," *European J. Appl. Microbiol.*, vol. 2, pp. 1–7 (1975).

Makover, et al., "New Mechanisms for the Biosynthesis and Metabolism of 2–Keto–L–Gulonic Acid in Bacteria," *Biotechnol. Bioeng*, vol. 17, pp. 1485–1514 (1975).

Hoshino, et al., "Isolation and Characterization of NAD(P)–Dependent L–Sorbosone Dehydrogenase from *Gluconobacter melanogenus* UV10," *Agric. Biol. Chem.*, vol. 55(3), pp. 665–670 (1991).

Kondo, et al., "Characterization of the Genes Encoding the Three–Component Membrane–Bound Alcohol Dehydrogenase from *Gluconobacter suboxydans* and Their Expression in *Acetobacter pasteurianus*," *Applied and Environmental Microbiology*, vol. 63, No. 3, pp. 1131–1138 (1997).

Matsushita, et al., "Function of Multiple Heme c Moieties in Intramolecular Electron Transport and Ubiquinone Reduction in the Quinohemoprotein Alcohol Dehydrogenase–Cytochrome c Complex of *Gluconobacter suboxydans*," *J. Biol. Chem.*, vol. 271, No. 9, pp. 4850–4857 (1996).

Thurner, et al., "Biochemical and Genetic Characterization of the Acetaldehyde Dehydrogenase Complex from *Acetobacter europaeus*," *Arch. Microbiol.*, vol. 168, No. 22, pp. 81–91 (1997).

*Primary Examiner*—Irene Marx
(74) *Attorney, Agent, or Firm*—Bryan Cave LLP

(57) ABSTRACT

A new aldehyde dehydrogenase having the physico-chemical properties: molecular weight:150,000±6,000 or 230,000±9,000; substrate specificity active on aldehyde compounds; cofactors:pyrroloquinoline quinone and heme c; optimum pH: 7.0–8.5; and inhibitors: $Co^{2+}$, $Cu^{2+}$, $Fe^{2+}$, $Ni^{2+}$, $Zn^{2+}$, monoiodoacetate and EDTA, is derived from a microorganism belonging to the genus *Gluconobacter*. Said aldehyde dehydrogenase can be produced by cultivating a microorganism of the genus *Gluconobacter* which is capable of producing an aldehyde dehydrogenase having the above properties, in an aqueous nutrient medium under aerobic conditions, disrupting the cells of the microorganism and isolating and purifying the aldehyde dehydrogenase from the cell-free extract of the disrupted cells of the microorganism. 2-Keto-L-gulonic acid (2-KGA) can be produced from L-sorbosone by contacting L-sorbosone with (i) the aldehyde dehydrogenase in the presence of an electron acceptor, (ii) a *Gluconobacter* microorganism capable of producing the aldehyde dehydrogenase in an aqueous medium under aerobic conditions or (iii) a cell-free extract of said microorganism, and in each case isolating the resulting 2-KGA from the reaction mixture.

3 Claims, 3 Drawing Sheets

METHOD OF MAKING AN ALDEHYDE DEHYDROGENASE WITH *GLUCONOBACTER*

This is a division of U.S. application Ser. No. 09/203,628, filed Dec. 1, 1998, now U.S. Pat. No. 6,242,233.

BACKGROUND OF THE INVENTION

The present invention concerns a novel enzyme, namely aldehyde dehydrogenase (ADH), a process for producing ADH and a process for producing 2-keto-L-gulonic acid (2-KGA) from L-sorbosone utilizing said enzyme. 2-KGA is an important intermediate for the production of vitamin C.

Some microorganisms are known to convert L-sorbosone to 2-KGA. For example, in U.S. Pat. No. 3,907,639, the microorganisms belonging to the genera Acetobacter, Pseudomonas, Escherichia, Serratia, Bacillus, Staphylococcus, Aerobacter, Alcaligenes, Penicillium, Candida and *Gluconobacter* are reported to be capable of effecting the conversion. Furthermore, Kitamura et al. (Eur. J. Appl. Microbiol., 2, 1, 1975) report that the enzyme oxidizing L-sorbosone found in *Gluconobacter melanogenus* IFO 3293 requires neither a coenzyme nor an electron acceptor for the development of enzyme activity. Makeover et al. (Biotechnol. Bioeng. 17, 1485, 1975) report the presence of L-sorbosone dehydrogenase activity in the particulate fraction of *Pseudomonas putida* ATCC 21812 and of *Gluconobacter melanogenus* IFO 3293. They also indicate that neither nicotinamide adenine dinucleotide (NAD) nor nicotinamide adenine dinucleotide phosphate (NADP) acts as a coenzyme for the enzyme. T. Hoshino et al. (Agric. Biol. Chem., 55, 665, 1991) purified and characterized L-sorbosone dehydrogenase from *Gluconobacter melanogenus* UV10, which requires NAD or NADP as a coenzyme.

In the context of the present invention, microorganisms belonging to the genus *Gluconobacter* have been studied more closely and, as a result, it has been found that the further novel ADH which catalyzes the oxidation of L-sorbosone to 2-KGA can be obtained from said microorganisms. Furthermore, it has been found that the purified ADH provided by the present invention oxidizes L-sorbosone to 2-KGA in the presence of electron acceptors, such as 2,6-dichlorophenolindophenol (DCIP) and phenazine methosulfate (PMS), ferricyanide or cytochrome c, but that NAD, NADP and oxygen are not suitable as electron acceptors. Thus, the ADH provided by the present invention is clearly distinct from the known L-sorbosone dehydrogenase.

SUMMARY OF THE INVENTION

This invention provides a purified aldehyde dehydrogenase, wherein the dehydrogenase: has a molecular weight of 150,000 ±6,000 Da and comprises two homologous subunits or has a molecular weight of 230,000 ±9,000 Da and comprises three homologous subunits, each subunit having a molecular weight of about 75,000 ±3,000 Da; has L-sorbosone, D-glucosone, D-glucose, D-galactose, D-mannose, L-gulose, D-xylose, D-ribose, and D-arabinose dehydrogenase activity; utilizes as cofactors pyrroloquinoline quinone and heme c; has an optimum pH of from 7.0 to 8.5;and is inhibited by $Co^{2+}$, $Cu^{2+}$, $Fe^{2+}$, $Ni^{2+}$, $Zn^{2+}$, monoiodoacetate and ethylenediamine tetraacetic acid.

This invention provides a process for producing the aldehyde dehydrogenase described above, comprising disrupting one or more cells of a *Gluconobacter* organism containing the dehydrogenase, and purifying the aldehyde dehydrogenase from the disrupted cells.

This invention provides a process for producing a carboxylic acid from its corresponding aldehyde which comprises contacting the aldehyde with the purified aldehyde dehydrogenase of this invention, in the presence of an electron acceptor.

Data are expressed as a percentage of the activity of ADH enzyme in potassium phosphate buffer at pH 8.0. Filled circles represent ADH enzyme in 50 mM potassium phosphate buffer. Open circles represent ADH enzyme in 50 mM Tris-HCl buffer.

Figure 2:
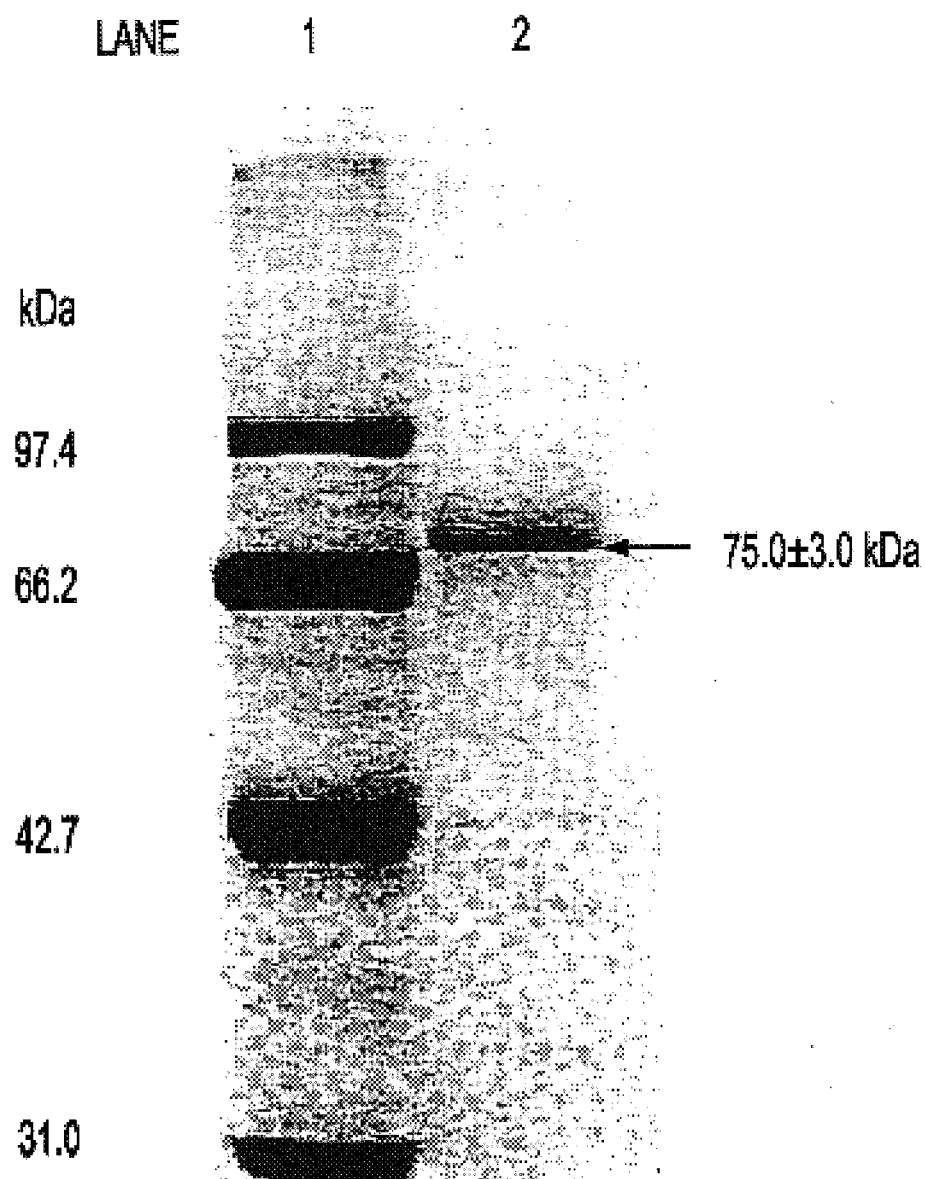

FIG. 2 SDS-PAGE Analysis of the Purified Aldehyde Dehydrogenase Enzyme

10% polyacrylamide gel, CBB staining. Lane 1: Molecular weight standards: phospholylase B, 97.4 k; bovine serum albumin, 66.2 k; ovalbumin, 42.7 k; bovine carbonic anhydrase, 31.0 k. Lane 2: The purified enzyme treated with SDS.

Figure 3:
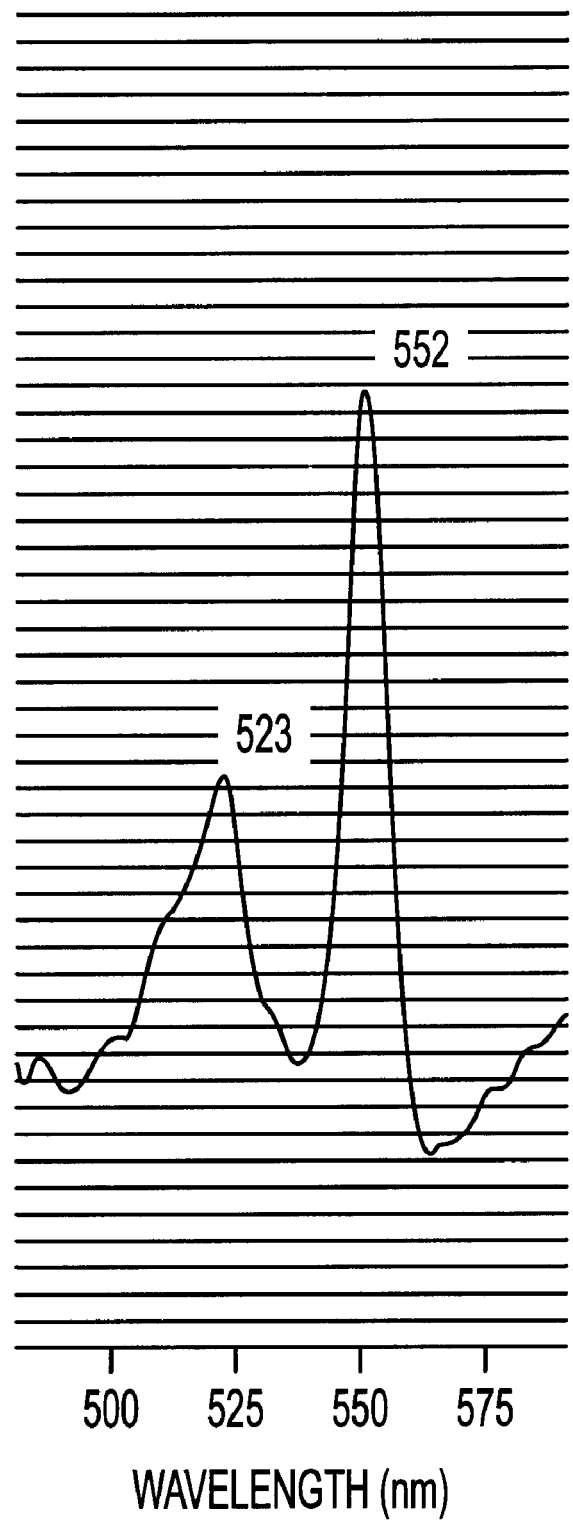

FIG. 3 Reduced minus oxidized difference spectrum of purified enzyme protein

DETAILED DESCRIPTION OF THE INVENTION

The present invention provides the novel ADH which acts on L-sorbosone to produce 2-KGA and has the following physico-chemical properties:

a) Molecular weight:150,000±6,000 or 230,000±9,000 (consisting of two or three homologous subunits, each having a molecular weight of about 75,000±3,000)

b) Substrate specificity: active on aldehyde compounds (See Tables 1A and 1B)

c) Cofactors:pyrroloquinoline quinone (PQQ) and heme c d) Optimum pH:7.0 to 8.5 e) Inhibitors:$Co^{2+}$, $Cu^{2+}$, $Fe^{2+}$, $Ni^{2+}$, $Zn^{2+}$, monoiodoacetate and ethylenediamine tetraacetic acid The source of the ADH is not critical. Thus, the ADH of this invention can be produced, for example, by isolation from a *Gluconobacter* or other organism or it can be produced recombinantly or by chemical synthesis.

The present invention also provides a process for producing the novel ADH of the invention, as defined above, by disrupting one or more cells of a microorganism belonging to the genus *Gluconobacter* which contain the ADH and purifying the ADH from the disrupted cells. In a specific embodiment of this invention the ADH is produced by cultivating a microorganism belonging to the genus *Gluconobacter*, which is capable of producing the ADH having the above properties; in an aqueous nutrient medium under aerobic conditions, disrupting the cells of the microorganism and isolating and purifying the ADH from the cell-free extract of the disrupted cells of the microorganism. In an embodiment this invention provides a process of producing the ADH of this invention, comprising disrupting one or more cells of a *Gluconobacter oxydans* microorganism having the identifying characteristics of *Gluconobacter oxydans* DSM No. 4025 (FERM BP-3812) which cell or cells contain the dehydrogenase, and purifying the aldehyde dehydrogenase from the disrupted cells.

In an embodiment, the present invention provides a process for producing 2-KGA from L-sorbosone utilizing the ADH of the present invention, which process comprises contacting L-sorbosone with (i) the ADH, as defined above, in the presence of an electron acceptor, or (ii) a microorganism belonging to the genus *Gluconobacter* which is capable of producing the ADH, as defined above, in an aqueous nutrient medium under aerobic conditions, or (iii) a cell-free extract of said microorganism, and in each of the cases (i), (ii) and (iii) isolating the resulting 2-KGA from the reaction mixture.

The physico-chemical properties of the purified sample of the ADH, prepared according to the Examples presented hereinafter, are as follows:

1) Enzyme Activity

The ADH of the present invention catalyzes the oxidation of L-sorbosone to 2-KGA in the presence of an electron acceptor according to the following reaction equation:

L-Sorbosone+Electron acceptor→2-KGA+Reduced electron acceptor

The enzyme does not work with oxygen as an electron acceptor. This was affirmed by the failure of the enzyme to convert L-sorbosone to 2-KGA using oxygen as a possible electron acceptor. Furthermore, no oxygen consumption was detected in the reaction mixture as detected with a dissolved oxygen probe. In addition NAD and NADP are not suitable electron acceptors. However, other conventional electron acceptors can be utilized in conjunction with the enzyme of this invention. DCIP, PMS, ferricyanide and cytochrome c are preferred electron acceptors. There is no minimum amount of electron acceptor which must be present for at least some of the aldehyde substrate to be converted to its corresponding acid. However, the amount of substrate which can be oxidized depends on the amount of the particular electron acceptor and its electron accepting characteristics.

The enzyme assay was performed as follows:

The reaction mixture for assaying the ADH activity consisted of 0.1 mM DCIP, 1.0 mM PMS, 50 mM potassium phosphate buffer (pH 8.0), 1.0 µM PQQ, 2.0 mM L-sorbosone and enzyme solution in a final volume of 100 µl with water, which reaction mixture was prepared just before the assay. The reaction was started at 25° C. with L-sorbosone, and the enzyme activity was measured as the initial reduction rate of DCIP at 600 nm. One unit of the enzyme activity was defined as the amount of the enzyme catalyzing the reduction of 1 µmole DCIP per minute. The extinction coefficient of DCIP at pH 8.0 was taken as 15 mM$^{-1}$. A reference cuvette contained all the above constituents except L-sorbosone.

The protein concentration was measured with the BCA protein assay reagent (Pierce Co., Rockford, Ill. 61105, U.S.A.).

2) Substrate specificity a) The substrate specificity of the enzyme was determined using the same enzyme assay method as described under 1) above, except that various substrate solutions (100 mM) were used instead of L-sorbosone. The relative activity of the ADH for D-glucosone, D-glucose, D-galactose, D-mannose, L-gulose, D-xylose, D-ribose and D-arabinose was higher than that for L-sorbosone. However, the relative activity for D,L-glyceraldehyde was lower than 1% of that for L-sorbosone. These results are presented in Table 1A:

TABLE 1A

Substrate specificity of the purified enzyme

| Substrate | Relative activity (%) |
|---|---|
| L-Sorbosone | 100.0 |
| D,L-Glyceraldehyde | <1 |
| D-Glucosone | 776.2 |
| D-Glucose | 864.2 |
| L-Sorbose | <1 |
| D-Galactose | 949.1 |
| D-Mannose | 1003.3 |
| L-Gulose | 684.5 |
| D-Sorbitol | <1 |
| D-Xylose | 1259.7 |
| D-Ribose | 803.9 |
| D-Arabinose | 298.9 | b) The products of the oxidation of the substrate indicated in Table 1A are shown in Table 1B below

TABLE 1B

| Substrate | Product |
|---|---|
| L-Sorbosone | 2-KGA |
| D-Glucosone | 2-Keto-D-gluconic acid |
| D-Glucose | D-Gluconate |
| D-Galactose | D-Galactonic acid |
| D-Mannose | D-Mannoic acid |
| L-Gulose | L-Gulonic acid |
| D-Xylose | D-Xylonic acid |
| D-Ribose | D-Ribonic acid |
| D-Arabinose | D-Arabonic acid |

3) Optimum pH

The correlation between the reaction rate of the ADH and pH values of the reaction mixture was determined by the same assay method as described under 1) above, except that various pHs and buffers were used.

Figure 1:
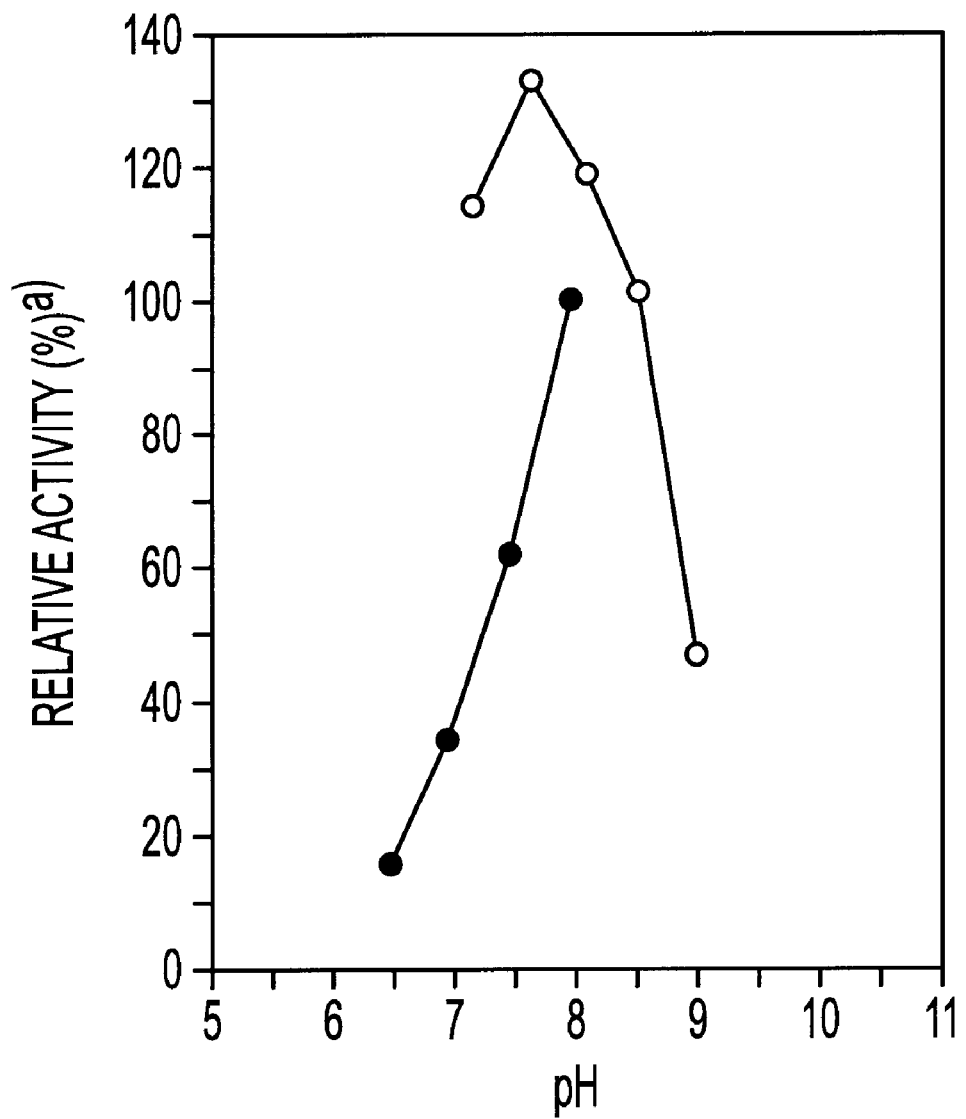
FIG. 1 Effect of pH on Activity of Purified Aldehyde Dehydrogenase Enzyme

The enzyme showed relatively high activity at pH 7.0 to 8.5, as shown in FIG. 1.

4) Thermostability

The thermostability of the enzyme was tested by incubating it for 5 minutes at various temperatures in 50 mM potassium phosphate buffer (pH 7.0). The residual activity was measured by the same enzyme assay method as described under 1) above, after which the treated enzyme was immediately cooled down in ice water. The enzyme was stable up to 45° C., but only about 30% of the activity remained after the treatment at 80° C. The results are shown in Table 2:

TABLE 2

Effect of temperature on the stability of the purified enzyme

| Temperature (° C.) | Relative activity (%) |
|---|---|
| 0 | 100.0 |
| 25 | 89.2 |
| 35 | 98.8 |
| 45 | 100.0 |
| 55 | 44.2 |
| 60 | 63.6 |
| 65 | 62.8 |
| 70 | 47.9 |
| 75 | 48.8 |
| 80 | 28.7 |

In this table the relative activities are expressed as percentages of the activity at 0° C.

5) Effects of Metal Ions and Inhibitors

The effects of metal ions and inhibitors on the activity of the enzyme were examined by measuring the activity using the same assay method as described under 1) above. Each compound solution was stirred into the basal reaction mixture and the reaction was started with the addition of the enzyme. The results are shown in Table 3:

TABLE 3

Effect of inhibitors and metals on the activity of the purified enzyme

| Compound | Relative activity (%) |
|---|---|
| None | 100.0 |
| EDTA | 14.6 |
| Quinine | 124.4 |
| KCN | 129.4 |
| $NaN_3$ | 104.6 |
| N-Ethylmaleimide | 110.8 |
| Monoiodoacetate | 52.2 |
| NaF | 86.7 |
| $CaCl_2.2H_2O$ | 204.5 |
| $CoCl_2.6H_2O$ | 76.0 |
| $CuSO_4$ | 0.0 |
| $Fe_2(SO_4)_3.xH_2O$ | 58.9 |
| $NiSO_4.6H_2O$ | 74.9 |
| $TiCl_4$ | 128.0 |
| $ZnCl_2$ | 40.3 |
| $MgCl_2$ | 90.3 |

Each compound was added to the reaction mixture at a concentration of 1.0 mM, except that the concentration of EDTA was 5.0 mM.

As shown in Table 3, the enzyme activity was stimulated by about 2-fold in the presence of 1.0 mM of $Ca^{2+}$, whereas $Co^{2+}$, $Cu^{2+}$, $Fe^{2+}$, $Ni^{2+}$, and $Zn^{2+}$ inhibited the enzyme activity. The addition of 5 mM ethylenediamine tetraacetic acid (EDTA) strongly inhibited the activity. However, the enzyme activity was slightly increased to 124% and 129% by the addition of 1.0 mM quinine and 1.0 mM KCN, respectively.

6) Molecular Weight

The molecular weight of the enzyme was measured with a size exclusion gel column (TSK-gel G3000 SWXL; Tosoh Co., Akasaka 1-7-7, Minato-ku, Tokyo, Japan). The enzyme showed two peaks corresponding to the apparent molecular weight of 150,000±6,000 and 230,000±9,000 on the chromatography. On analyzing this enzyme by SDS-polyacrylamide gel electrophoresis, it was shown that the enzyme consisted of the homologous subunit of molecular weight 75,000±3,000 (FIG. 2). This indicates that the enzyme consists of two or three homologous subunits. Both the dimeric and trimeric forms of the enzyme are active.

7) Prosthetic Group

The purified enzyme did not show the catalyzing activity for converting L-sorbosone to 2-KGA in the basal reaction mixture without PQQ. However, the activity of the enzyme was restored by the addition of PQQ in the reaction mixture or incubating the enzyme with PQQ and $Ca^{2+}$for 5 minutes.

The detection of heme c of the purified enzyme was performed by the reduced-minus-oxidized difference spectrum taken by a UV-VIS recording spectrophotometer (Shimadzu UV-2200; Shimadzu Co., Kuwahara-cho 1, Nishinokyo, Chukyo-ku, Kyoto, Japan). The enzyme was suspended in 50 mM potassium phosphate buffer (pH 7.0) at a concentration of 50 µg/ml and the enzyme of dithionite-reduced form and ammonium persulfate-oxidized form were prepared to measure the difference spectrum. The spectrum gave the difference maxima at 552 and 523 nm, as shown in FIG. 3. The result strongly suggests that the enzyme has heme c as a prosthetic group.

8) Effect of Substrate Concentration

The velocity of the oxidizing reaction with various concentrations of L-sorbosone from 1 mM to 8 mM was measured to determine the Km value for L-sorbosone. The Michaelis constant was calculated to be 17.8 mM from the Lineweaver-Burk plot based on the reaction velocity when DCIP was used as the electron acceptor for the reaction.

9) Purification Procedure

The purification of the enzyme is effected by any combination of known purification methods, such as ion exchange chromatography, gel-electrophoresis, salting out and dialysis.

The enzyme provided by the present invention can be prepared by cultivating an appropriate microorganism in an aqueous nutrient medium under aerobic conditions, disrupting the cells of the microorganism and isolating and purifying the aldehyde dehydrogenase from the cell-free extract of the disrupted cells of the microorganism.

The microorganisms used for the process of the present invention are microorganisms belonging to the genus *Gluconobacter* which are capable of producing aldehyde dehydrogenase as defined hereinbefore. Functional equivalents, subcultures, mutants and variants of the said microorganism, including functional equivalents, subcultures, mutants and variants of *Gluconobacter oxydans* DSM No. 4025 can also be used in the present invention. Strains which are derived from *Gluconobacter oxydans* DSM 4025 or DSM 4025 (FERM BP-3812) can be used as well.

A preferred strain is *Gluconobacter oxydans*. The strain most preferably used in the present invention is *Gluconobacter oxydans* DSM 4025, which was deposited at the Deutsche Sammlung von Mikroorganismen in Göttingen (Germany), based on the stipulations of the Budapest Treaty, under DSM No. 4025 on Mar. 17, 1987. The depositor was The Oriental Scientific Instruments Import and Export Corporation for Institute of Microbiology, Academia Sinica, 52 San-Li-He Rd., Beijing, Peoples Republic of China. The effective depositor was said Institute, of which the full address is The Institute of Microbiology, Academy of Sciences of China, Haidian, Zhongguancun, Beijing 100080, People's Republic of China.

Moreover, a subculture of the strain has also been deposited at the National Institute of Bioscience and Human-Technology, Agency of Industrial Science and Technology, Japan, also based on the stipulations of the Budapest Treaty, under the deposit No. *Gluconobacter oxydans* DSM No. 4025 (FERM BP-3812) on Mar. 30, 1992. The depositor was the Nippon Roche Research Center, 200 Kajiwara Aza Sotokochi, Kamakura-shi, Kanagawa-ken 247, Japan. This subculture is also most preferably used in the present invention.

Furthermore, European Patent Publication No. 0 278 447 discloses the characteristics of this strain, as follows:

a) 2-Keto-L-gulonic acid is produced from sorbose, b) ethanol is oxidized to acetic acid, c) D-glucose is oxidized to D-gluconic acid and 2-keto-D-gluconic acid, d) ketogenesis of polyalcohols, e) pellicle and ring growth in mannitol broth (24 hrs cultivation) at pH 4 and 5, and pellicle growth in glucose broth at pH 4.5.

f) glycerol is not substantially oxidized to dihydrooxyacetone, g) 2-keto-D-glucaric acid is produced from sorbitol and glucaric acid but not from glucose, fructose, gluconic acid, mannitol or 2-keto-D-gluconic acid, h) polymorphic, apparently no flagella,
i) brown pigment is produced from fructose,
j) good growth when co-cultured in the presence of *Bacillus megaterium* or a cell extract thereof,
k) streptomycin sensitive.

The microorganism may be cultured in an aqueous medium supplemented with appropriate nutrients under aerobic conditions. The cultivation may be conducted at a pH of 4.0 to 9.0, preferably 6.0 to 8.0. The cultivation period varies depending on the pH, temperature and nutrient medium to be used, and is preferably about 1 to 5 days. The preferred temperature range for carrying out the cultivation is from about 13° C. to about 36° C., preferably from 18° C. to 33° C.

It is usually required that the culture medium contains such nutrients as assimilablècarbon sources, for example glycerol, D-mannitol, D-sorbitol, erythritol, ribitol, xylitol, arabitol, inositol, dulcitol, D-ribose, D-fructose, D-glucose and sucrose, preferably D-sorbitol, D-mannitol and glycerol; and digestible nitrogen sources such as organic substances, for example, peptone, yeast extract, baker's yeast, urea, amino acids and corn steep liquor. Various inorganic substances may also be used as nitrogen sources, for example nitrates and ammonium salts. Furthermore, the culture medium usually contains inorganic salts, for example magnesium sulfate, potassium phosphate and calcium carbonate.

An embodiment for the isolation and purification of the ADH from the microorganism after the cultivation is briefly described hereinafter:

(1) Cells are harvested from the liquid culture broth by centrifugation or filtration.
(2) The harvested cells are washed with water, physiological saline or a buffer solution having an appropriate pH.
(3) The washed cells are suspended in the buffer solution and disrupted by means of a homogenizer, sonicator or French press or by treatment with lysozyme and the like to give a solution of disrupted cells.
(4) The ADH is isolated and purified from the cell-free extract of disrupted cells, preferably from the cytosol fraction of the microorganism.

A cell-free extract can be obtained from the disrupted cells by any conventional technique, including but not limited to centrifugation.

The ADH provided by the present invention is useful as a catalyst for the production of 2-KGA from L-sorbosone. The reaction should be conducted at pH values of about 6.5 to about 9.0 in the presence of an electron acceptor, for example DCIP, PMS and the like in a solvent such as phosphate buffer, Tris-buffer and the like. When the pH and temperature are set at about 7.5 to 8.5 and about 25° C., respectively, the reaction usually produces the best results.

The concentration of L-sorbosone in a solvent can vary depending upon other reaction conditions but, in general, is about 0.5 to 50 g/l, most preferably from about 1 to about 30 g/l.

In the reaction, the ADH may also be used in an immobilized state with an appropriate carrier. Any means of immobilizing enzymes generally known in the art may be used. For instance, the enzyme may be bound directly to a membrane, granules or the like of a resin having one or more functional groups, or it may be bound to the resin through bridging compounds having one or more functional groups, for example glutaraldehyde.

In addition to the above, the cultured cells are also useful for the production of carboxylic acids from aldehydes, especially for the production of 2-KGA from L-sorbosone. The production of other carboxylic acids from their corresponding aldehydes is carried out under the same conditions, including substrate concentration, as the conversion of L-sorbosone to 2-KGA as described above.

The following Example further illustrates the present invention.

EXAMPLE

Preparation of ADH

All the operations were performed at 8° C., and the buffer was 0.05 M potassium phosphate (pH 7.0) unless otherwise stated.

(1) Cultivation of *Gluconobacter oxydans* DSM No. 4025 (FERM BP-3812)

*Gluconobacter oxydans* DSM 4025 (FERM BP-3812) was grown on an agar plate containing 5.0% D-mannitol, 0.25% $MgSO_4 \cdot 7H_2O$, 1.75% corn steep liquor, 5.0% baker's yeast, 0.5% urea, 0.5% $CaCO_3$ and 2.0% agar at 27° C. for 4 days. One loopful of the cells was inoculated into 50 ml of a seed culture medium containing 2% L-sorbose, 0.2% yeast extract, 0.05% glycerol, 0.25% $MgSO_4 \cdot 7H_2O$, 1.75% corn steep liquor, 0.5% urea and 1.5% $CaCO_3$ in a 500 ml Erlenmeyer flask, and cultivated at 30° C. with 180 rpm for one day on a rotary shaker. 10 ml samples of this culture were transferred into 500 ml Erlenmeyer flasks containing 100 ml of the same seed culture medium and cultivated in the same manner as described above. The seed culture thus prepared was used for inoculating 15 liters of medium, which contained 8.0% L-sorbose, 0.05% glycerol, 0.25% $MgSO_4 7H_2O$, 3.0% corn steep liquor, 0.4% yeast extract and 0.15% antifoam, in 30 l jar fermentor. The fermentation parameters were 800 rpm for the agitation speed and 0.5 vvm (volume of air/volume of medium/minute) for aeration at a temperature of 30° C. The pH was maintained at 7.0 with sodium hydroxide during the fermentation. After 48 hours of cultivation, 30 liters of the cultivated broth containing the cells of *Gluconobacter oxydans* DSM No. 4025 (FERM BP-3812) by using the two sets of fermentors were harvested by continuous centrifugation. The pellets containing the cells were recovered and suspended in an appropriate volume of saline. After the suspension had been centrifuged at 2,500 rpm (1,000×g), the supernatant containing the slightly reddish cells was recovered to remove the insoluble materials derived from corn steep liquor and yeast extract which were ingredients in the medium. The supernatant was then centrifuged at 8,000 rpm (10,000×g) to obtain the cell pellet. As a result, 123 g of the wet weight of cells of *Gluconobacter oxydans* DSM No. 4025 (FERM BP-3812) were obtained from 30 liters of broth.

(2) Preparation of cytosol fraction

The cell paste (55 g) was suspended with 100 ml of the buffer and passed through a French pressure cell press. After centrifugation to remove intact cells, the supernatant was designated as the cell-free extract, and the cell-free extract was centrifuged at 100,000×g for 90 minutes. The resultant supernatant (165 ml) was designated as the soluble fraction of *Gluconobacter oxydans* DSM No. 4025 (FERM BP-3812). After this fraction had been dialyzed against the buffer, 126 ml of the dialyzed fraction having the specific activity on L-sorbosone of 2.26 units/mg protein were used for the next purification step.

(3) Diethylaminoethyl (DEAE)-cellulose column chromatography

The dialysate (126 ml) was put on a column of DEAE-cellulose (Whatman DE-52, 3×50 cm; Whatmann BioSystems Ltd., Springfield MIII, James Whatman Way, Maidstone, Kent, U.K.) equilibrated with the buffer and washed with the buffer to elute minor proteins. Then a linear gradient elution with NaCl from 0.3 to 0.8 M in the buffer was carried out. Major enzyme activity was eluted at NaCl concentrations ranging from 0.32 to 0.36 M. The active fractions (116 ml) were collected and dialyzed against the buffer.

(4) DEAE-sepharose column chromatography

A 60 ml portion of the dialyzed active fraction from the previous step was introduced into a column of DEAE-sepharose CL-6B (Pharmacia, 1.5×50 cm; Amersham Pharmacia Biotech AB, S-75184 Uppsala, Sweden) equilibrated with the buffer. After the column had been washed with the buffer containing 0.2 M NaCl, a linear gradient of NaCl from 0.2 to 0.6 M was added to the buffer. The active fractions were eluted at NaCl concentrations ranging from 0.44 to 0.47 M.

(5) Q-sepharose column chromatography

A portion (13.5 ml) of the pooled active fractions (53 ml) from the previous step was added with appropriate volume of the buffer to decrease the concentration of NaCl, and introduced into a column of Q-sepharose (Pharmacia, 1.0 by 20 cm) equilibrated the buffer. After the column had been washed with the buffer containing 0.35 M NaCl, a linear gradient of NaCl from 0.35 to 0.5 M was added to the buffer. The activities corresponding to the ADH were eluted at NaCl concentrations ranging from 0.39 to 0.40 M. The active fractions (30 ml) collected were ultrafiltrated by an ultrafiltrator (Centriprep-10, Amicon; Amicon Inc. Cherry Hill Drive, Beverly, Mass. 01915, U.S.A.) to concentrate and desalt. As a result, 700 $\mu$l of the concentrated active fraction were obtained.

(6) Native polyacrylamide gel electrophoresis (Native PAGE)

A 600 $\mu$l portion of the enzyme fraction from the previous step was applied on a native polyacrylamide gel (10%, pH 9.4, 10 by 10 cm). The electrophoresis was performed at 30 mA and 4° C. for 1.5 hours. The enzyme band corresponding to the active fraction was excised from the gel, and the enzyme was electrically eluted from the gel into the Tris glycine buffer (pH 8.3) by using a MAX-YIELD Protein Concentrator (Atto Co., Hongo 1-25-23, Bunkyo-ku, Tokyo, Japan) at 10 W and 4° C. for 3 hours. The enzyme solution was concentrated 4-fold using an ultramembrane filter (Centricon-10, Amicon), and the buffer was changed to 50 mM potassium phosphate buffer (pH 7.0). Then the enzyme solution was stored at −30° C.

A summary of the purification steps of the enzyme is given in Table 4.

TABLE 4

Purification of the aldehyde dehydrogenase from *Gluconobacter oxydans* DSM No. 4025 (FERM BP-3812)

| Step | Total activity (units) | Total protein (mg) | Specific activity (units/mg protein) |
|---|---|---|---|
| Soluble fraction | 5994.2 | 2652.3 | 2.26 |
| DEAE-Cellulose DE52 | 4206.9 | 594.2 | 7.08 |
| DEAE-Sepharose CL-6B | 1640.5 | 107.9 | 15.29 |
| Q-Sepharose | 243.3 | 11.84 | 20.55 |
| Native PAGE | 193.8 | 3.59 | 53.98 |

(7) Purity of the Isolated Enzyme

The purified enzyme with a specific activity of 54.0 units per mg protein (0.62 mg/ml) was used for the following analysis:

The molecular weight of the native enzyme was determined by high performance liquid chromatography using a size exclusion gel column (TSK gel G3000 SWXL column, 7.8×300 mm) equilibrated with 0.1 M potassium phosphate buffer (pH 7.0) containing 0.3 M NaCl at 280 nm and a flow rate of 1.5 ml per minute. Cyanocobalamin (1.35 K), myoglobin (17 K), ovalbumin (44 K), γ-globulin (158 K) and thyroglobulin (670 K) were used as molecular weight standards. The purified enzyme showed two peaks having the molecular weights 150,000±6,000 and 230,000±9,000.

However, in the presence of sodium dodecyl sulfate (SDS), the enzyme showed a single band with a molecular weight of 75,000±3,000. From these results, the purified enzyme consisted of two or three homologous subunits.

(8) Identification of the Reaction Product

The reaction mixture containing the purified enzyme (1.56 mg), L-sorbosone (0.142 mg), PMS (0.008 mg) and PQQ (0.3 mg) in 40$\mu$l of the buffer was incubated for 1.5 hours at 30° C. The reaction product was analyzed on thin layer chromatography and HPLC. As a result, the reaction product was identified as 2-KGA in comparison with an authentic sample of 2-KGA.

What is claimed is:

1. A process for producing an aldehyde dehydrogenase wherein the dehydrogenase has a molecular weight of 150,000±6,000 Da and comprises two homologous subunits or has a molecular weight of 230,000±9,000 Da and comprises three homologous subunits, each subunit having a molecular weight of about 75,000±3,000 Da;

has L-sorbosone, D-glucosone, D-glucose, D-galactose, D-mannose, L-gulose, D-xylose, D-ribose, and D-arabinose dehydrogenase activity;

utilizes as cofactors pyrroloquinoline quinone and heme c;

has an optimum pH from 7.0 to 8.5; and is inhibited by $Co^{2+}$, $Cu^{2+}$, $Fe^{2+}$, $NI^{2+}$, $Zn^{2+}$, monoiodoacetate and ethylenediamine tetraacetic acid, which process comprises cultivating cells of a *Gluconobacter* microorganism containing aldehyde dehydrogenase in an aqueous nutrient medium under aerobic conditions; disrupting the cells of the cultivated *Glucanobacter* microorganism and purifying the aldehyde dehydrogenase from the disrupted cells.

2. The process according to claim 1, wherein the microorganism is *Gluconobacter oxydans* DSM No. 4025.

3. The process according to claim 1, wherein the microorganism is *Gluconobacter oxydans* DSM No. 4025 FERM BP-3812.

* * * * *